US009364146B2

(12) United States Patent
Uchiyama

(10) Patent No.: US 9,364,146 B2
(45) Date of Patent: Jun. 14, 2016

(54) SLIT LAMP MICROSCOPE

(75) Inventor: Takumi Uchiyama, Tokyo (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 305 days.

(21) Appl. No.: 14/122,877

(22) PCT Filed: May 16, 2012

(86) PCT No.: PCT/JP2012/062464
§ 371 (c)(1),
(2), (4) Date: Nov. 27, 2013

(87) PCT Pub. No.: WO2012/172907
PCT Pub. Date: Dec. 20, 2012

(65) Prior Publication Data
US 2014/0139807 A1 May 22, 2014

(30) Foreign Application Priority Data
Jun. 14, 2011 (JP) ................................. 2011-132372

(51) Int. Cl.
A61B 3/10 (2006.01)
A61B 3/135 (2006.01)
(52) U.S. Cl.
CPC ...................................... A61B 3/135 (2013.01)
(58) Field of Classification Search
CPC ....................................................... A61B 3/135
USPC .................................................. 351/205, 214
See application file for complete search history.

(56) References Cited

U.S. PATENT DOCUMENTS

| 5,424,788 A | 6/1995 | Satake et al. |
| 6,283,596 B1 | 9/2001 | Yoshimura et al. |
| 2004/0004694 A1 | 1/2004 | Sugino et al. |

(Continued)

FOREIGN PATENT DOCUMENTS

| EP | 1872713 A1 | 1/2008 |
| EP | 2248460 A1 | 11/2010 |
| JP | S56-72841 A | 6/1981 |

(Continued)

OTHER PUBLICATIONS

International Search Report for Application No. PCT/JP2012/062464 dated Jun. 26, 2012.

(Continued)

Primary Examiner — Mahidere Sahle
(74) Attorney, Agent, or Firm — Pearne & Gordon LLP

(57) ABSTRACT

A slit lamp microscope capable of appropriately and easily carrying out the setting of the optical system is provided. In storage 102 of a slit lamp microscope 1, correspondence information 110 is stored in which standard setting conditions of an illumination system 8 and/or an observation system 6 are associated with each of multiple sites of an eye E. A searching part 121 searches the standard setting conditions corresponding to a site designated by an operation part 104 from the correspondence information 110. A setting-state acquiring part 122 acquires current setting states of the illumination system 8 and/or the observation system 6. A setting-state specifying part specifies, from among the current setting states acquired by the setting-state acquiring part 122, those differing from the standard setting conditions searched by the searching part 121. A controller displays information based on this specified result on the display 103.

15 Claims, 6 Drawing Sheets

(56) References Cited

U.S. PATENT DOCUMENTS

2004/0046941 A1  3/2004  Yamamoto
2010/0328608 A1  12/2010  Fujii et al.

FOREIGN PATENT DOCUMENTS

| | | |
|---|---|---|
| JP | 04-336030 A | 11/1992 |
| JP | 05-31078 A | 2/1993 |
| JP | 08-112257 A | 5/1996 |
| JP | 10-085189 A | 4/1998 |
| JP | 2001-037725 A | 2/2001 |
| JP | 2001-37726 A | 2/2001 |
| JP | 2003-310556 A | 11/2003 |
| JP | 2004-194689 A | 7/2004 |
| JP | 2005-065813 A | 3/2005 |
| JP | 2006330040 A | 12/2006 |
| JP | 2008-005987 A | 1/2008 |
| JP | 2009-178459 A | 8/2009 |

OTHER PUBLICATIONS

European Extended Search Report for EP12800500 Oct. 20, 2014.
JP2013-520478 Office Action of Apr. 12, 2016.

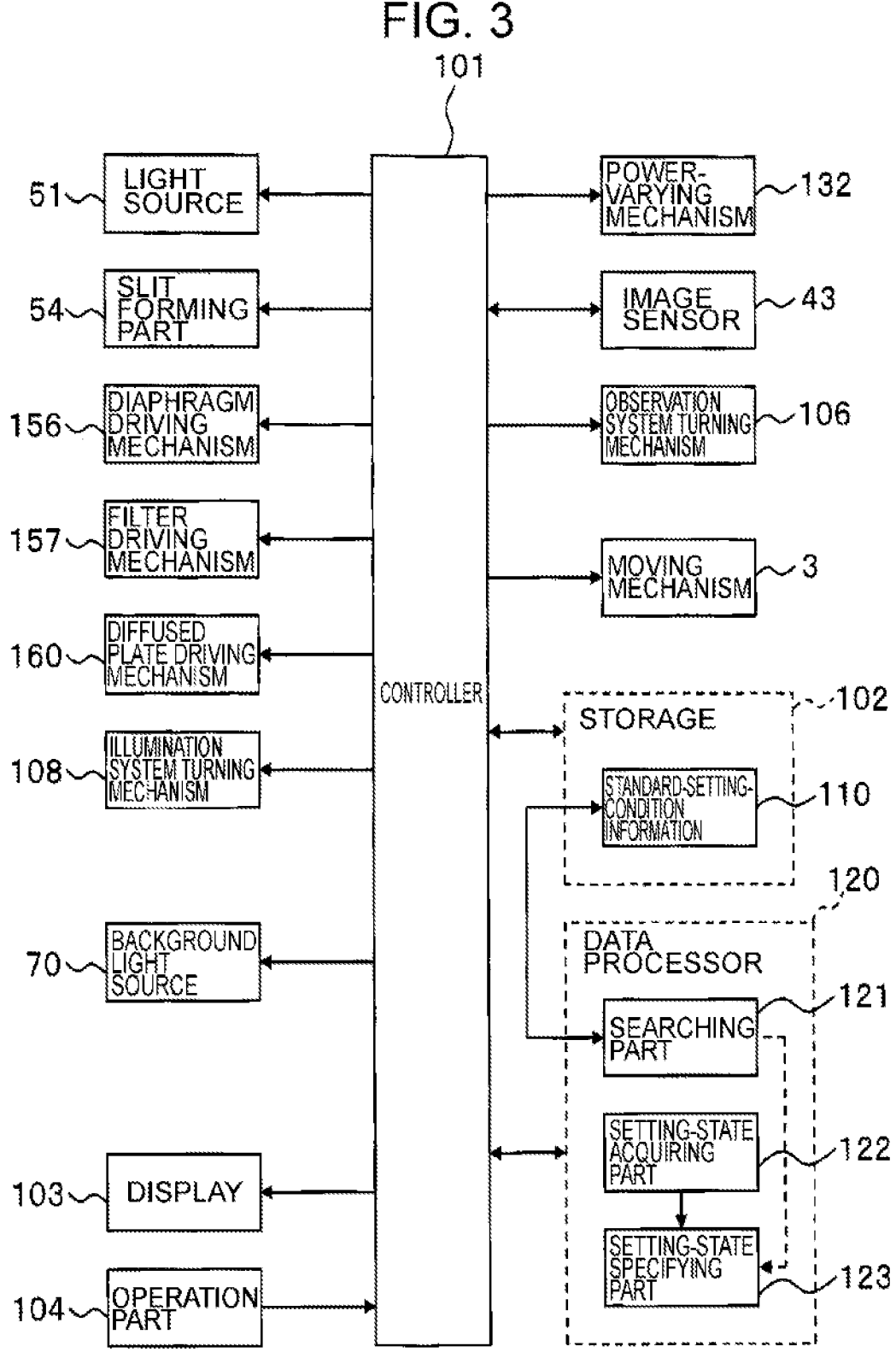

FIG. 4

| SITE | ANTERIOR SEGMENT | CONJUNCTIVA | CORNEA | CORNEA | CORNEA | CORNEA | IRIS | CRYSTALLINE LENS | CRYSTALLINE LENS | CORNER ANGLE | VITREOUS BODY | RETINA |
|---|---|---|---|---|---|---|---|---|---|---|---|---|
| OBSERVATION TECHNIQUE | DIFFUSED ILLUMINATION | DIFFUSED ILLUMINATION | DIFFUSED ILLUMINATION | DIRECT ILLUMINATION | BACKGROUND ILLUMINATION | FLUORESCENT STAINING | TANGENT ILLUMINATION | DIRECT ILLUMINATION | DIAPHANOSCOPY | GONIOSCOPE | DIRECT ILLUMINATION | ATTACHMENT LENS |
| MAGNIFICATION | 16 | 16 | 16 | 16 | 25 | 16 | 25 | 16 | 25 | 25 | 16 | 25 |
| SLIT WIDTH | FULL OPEN | FULL OPEN | FULL OPEN | EXTREMELY THIN | MEDIUM | FULL OPEN | MEDIUM-FULL OPEN | EXTREMELY THIN | WIDE | WIDE | THIN | WIDE |
| AMOUNT OF LIGHT | 3~4 | 1~2 | 3~4 | 4~5 | 3~4 | 4~5 | 2~3 | 4~5 | 3~4 | 2~3 | 3~5 | 3~5 |
| ILLUMINATING ANGLE | 10~30° | 10~30° | 10~30° | 30~90° | 30~60° | 10~30° | 30~90° | 30~60° | 0° | 0~10° | 0~30° | 0~10° |
| BACKGROUND ILLUMINATION | ABSENT | ABSENT | ABSENT | ABSENT | PRESENT | ABSENT | ABSENT | PRESENT | PRESENT | ABSENT | ABSENT | ABSENT |
| DIFFUSED PLATE | PRESENT | PRESENT | PRESENT | ABSENT | ABSENT | PRESENT | PRESENT/ABSENT | ABSENT | ABSENT | ABSENT | ABSENT | ABSENT |
| FILTER | ABSENT | ABSENT | ABSENT | ABSENT | ABSENT | PRESENT | ABSENT | ABSENT | ABSENT | ABSENT | ABSENT | ABSENT |

OBSERVATION TARGET SITE : CORNEA

| OBSERVATION TECHNIQUE | MAGNIFICATION | SLIT WIDTH | AMOUNT OF LIGHT | ILLUMINATING ANGLE | BACKGROUND ILLUMINATION | DIFFUSED PLATE |
|---|---|---|---|---|---|---|
| CURRENT SETTING | 25 | FULL OPEN | 1 | 20° | ABSENT | ABSENT |
| DIFFUSED ILLUMINATION | 16 | EXTREMELY THIN | 3~4 | | | PRESENT |
| DIRECT ILLUMINATION | 16 | MEDIUM | 4~5 | 30~90° | | |
| BACKGROUND ILLUMINATION | | | 3~4 | 30~60° | PRESENT | |
| FLUORESCENT STAINING | 16 | | 4~5 | | | PRESENT |

CHANGE OF SETTINGS

SLIT LAMP MICROSCOPE

FIELD OF THE INVENTION

The present invention relates to a slit lamp microscope.

BACKGROUND TECHNOLOGY

A slit lamp microscope is an ophthalmology device for illuminating an eye with slit light to carry out magnifying observation of this illumination field (for example, refer to Patent Document 1). It should be noted that "observation" includes at least one from among observation with naked eyes and imaging by an image sensor.

Slit lamp microscopes are used for observing various parts of an eye. Observation targets may include the entire anterior segment of the eye, cornea, sclera, iris, crystalline lens, conjunctiva, eye chamber, corner angle, vitreous body, retina, etc.

Moreover, various observation techniques exist that use slit lamp microscopes. Examples may include the diffused illumination method, direct illumination method, background illumination method, fluorescent staining photographing, tangent illumination method, diaphanoscopy, photographing using gonioscope, photographing using attachment lens, etc. The diffused illumination method is an observation technique carried out by irradiating an eye with diffused light obtained using a diffusing lens and/or diffusing plate. The direct illumination method is an observation technique carried out by irradiating an eye with light from the light source that is not diffused etc. The background illumination method is an observation technique carried out by irradiating the vicinity of an observation target with illumination light and illuminating the observation target by the reflected light thereof. Fluorescent staining photographing is an observation technique carried out by staining an eye with a fluorescent contrast medium (fluorescein) and irradiating illumination light via a blue filter. The tangent illumination method is an observation technique carried out by irradiating illumination light from the lateral side with respect to an observation target. Diaphanoscopy is an observation technique carried out by irradiating slit light from the margin of the pupil such that reflection from a fundus is maximized. Photographing using a gonioscope is an observation technique carried out by arranging the gonioscope on the cornea of an eye and irradiating the corner angle. Photographing using an attachment lens is an observation technique carried out by irradiating a fundus using a three-sided mirror, aspherical lens, etc. It should be noted that, in examinations using a slit lamp microscope, observation targets and observation techniques are arbitrarily combined and applied.

PRIOR ART DOCUMENTS

Patent Documents

[Patent Document 1] Japanese Published Unexamined Application 2009-178459

SUMMARY OF THE INVENTION

Problem to be Solved by the Invention

In examinations using a slit lamp microscope, in accordance with the selection of an observation target and/or an observation technique, settings of the optical system, for example: irradiation angle; amount of illumination light; observation magnification; slit width; filter; exposure (light sensitivity, shutter speed, diaphragm value (f-stop)), etc.); etc., are necessarily and appropriately changed.

If such settings of the optical system are not appropriately carried out, good images are not obtained, increasing the burden on the tester as well as the subject as a result of having to conduct retakes, prolonging the examination time, etc.

On the other hand, it is difficult to appropriately perform the setting of the optical system in accordance with the various combinations of observation targets and/or observation techniques, in addition to being troublesome to switch the settings each time when the observation targets and/or observation techniques are changed. Such problems become particularly prominent when the tester is unskilled in examinations using a slit lamp microscope.

The present invention was devised in order to solve the problems mentioned above, and the objective thereof is to provide a slit lamp microscope capable of appropriately and easily carrying out the setting of the optical system.

Means for Solving the Problem

In order to achieve the aforementioned objective, an invention described in claim 1 is a slit lamp microscope, comprising: an illumination system configured to include: a light source that outputs illumination light; a slit forming part that forms a slit capable of changing the slit width; a diffusion member that is capable of inserting into and removed from a light path of the illumination light and diffuses the illumination light; and a filter that is capable of inserting into and removed from the light path, wherein the illumination light having passed through the slit is irradiated to an eye and the amount as well as the irradiation angle of the illumination light are changeable, a background illumination system configured to irradiate background illumination light to a peripheral region of an irradiation field of the illumination light; an observation system configured to include a magnification optical system for changing observation magnification, and guide reflected light of the illumination light from the eye to each of an image sensor and an eyepiece; a display; a storage configured to store correspondence information that associates, with each of multiple sites of an eye, standard setting conditions regarding at least one of: a value of the observation magnification; a value of the slit width; a value of the light amount of the illumination light; a value of the irradiation angle; the presence or absence of irradiation of the background illumination light; the presence or absence of the diffusion member in the light path; and the presence or absence of the filter in the light path; a designating part configured to designate a site of the eye; a searching part configured to search the standard setting conditions corresponding to the designated site from the correspondence information; an acquiring part configured to acquire current setting states regarding at least one of: a value of the observation magnification; a value of the slit width; a value of the light amount of the illumination light; a value of the irradiation angle; the presence or absence of irradiation of the background illumination light; the presence or absence of the diffusion member in the light path; and the presence or absence of the filter in the light path; a specifying part configured to specify, from among the acquired current setting states, those differing from the searched standard setting conditions; and a controller configured to display information based on the specified result by the specifying part on the display.

An invention described in Claim 2 is a slit lamp microscope, comprising: an illumination system configured to include a light source that outputs illumination light and a slit forming part that forms a slit capable of changing the slit width, wherein the illumination light having passed through the slit is irradiated to an eye and the amount as well as the irradiation angle of the illumination light are changeable; an observation system configured to include a magnification optical system for changing observation magnification, and guide reflected light of the illumination light from the eye to each of an image sensor and an eyepiece: a display; a storage configured to store correspondence information that associates, with each of multiple sites of an eye, standard setting conditions of the illumination system and/or the observation system; a designating part configured to designate a site of the eye; a searching part configured to search the standard setting conditions corresponding to the designated site from the correspondence information; an acquiring part configured to acquire current setting states of the illumination system and/ or the observation system; a specifying part configured to specify, from among the acquired current setting states, those differing from the searched standard setting conditions; and a controller configured to display information based on the specified result by the specifying part on the display.

An invention described in Claim 3 is the slit lamp microscope according to Claim 1 or Claim 2, wherein the controller displays, as the information based on the specified result, the specified current setting states in a different manner from the current setting states that coincide with the standard setting conditions.

An invention described in Claim 4 is the slit lamp microscope according to Claim 1 or Claim 2, wherein the controller controls the illumination system and/or the observation system based on the searched standard setting conditions, thereby changing the specified current setting states.

An invention described in Claim 5 is the slit lamp microscope according to Claim 4, comprising a moving mechanism configured to horizontally move the illumination system and the observation system, wherein the acquiring part acquires the horizontal positions of the illumination system and the observation system as the current setting states, and the controller changes the specified current setting states based on the acquired positions.

An invention described in Claim 6 is the slit lamp microscope according to Claim 4, wherein the controller displays, together with the information based on the specified result, an operation key used for inputting instructions for changing the specified current setting states on the display, and the controller changes the current setting states in accordance with the operation key being operated.

An invention described in Claim 7 is the slit lamp microscope according to Claim 1 or Claim 2, wherein in the correspondence information, the standard setting conditions regarding at least one observation technique are associated with each of the multiple sites, and the controller displays the information based on the specified result for each observation technique associated with the designated site.

An invention described in Claim 8 is the slit lamp microscope according to Claim 2, wherein in the correspondence information, the standard setting conditions regarding at least one from among the value of the observation magnification, the value of the slit width, the value of the light amount of the illumination light, and the value of the irradiation angle are associated with each of the multiple sites, and the acquiring part acquires the current setting states regarding each of: the value of the observation magnification, the value of the slit width, the value of the light amount of the illumination light, and the value of the irradiation angle.

An invention described in Claim 9 is the slit lamp microscope according to Claim 8, wherein the illumination system includes a diffusion member that is capable of inserting into and removed from a light path of the illumination light and diffuses the illumination light, in the correspondence information, the standard setting conditions regarding the presence or absence of the diffusion member in the light path are associated with each of the multiple sites, and the acquiring part acquires the current setting states regarding the presence or absence of the diffusion member in the light path.

An invention described in Claim 10 is the slit lamp microscope according to Claim 8, comprising a background illumination system configured to irradiate background illumination light to a peripheral region of an irradiation field of the illumination light, wherein in the correspondence information, the standard setting conditions regarding the presence or absence of irradiation of the background illumination light are associated with each of the multiple sites, and the acquiring part acquires the current setting states regarding the presence or absence of irradiation of the background illumination light.

An invention described in Claim 11 is the slit lamp microscope according to Claim 8, wherein the illumination system includes a filter that is capable of inserting into and removed from the light path, in the correspondence information, the standard setting conditions regarding the presence or absence of the filter in the light path are associated with each of the multiple sites, and the acquiring part acquires the current setting states regarding the presence or absence of the filter in the light path.

An invention described in Claim 12 is the slit lamp microscope according to Claim 1 or Claim 8, wherein the illumination system includes an illumination diaphragm capable of changing the diaphragm value, in the correspondence information, the standard setting conditions regarding the diaphragm value are associated with each of the multiple sites, and the acquiring part acquires the current setting states regarding the diaphragm value.

An invention described in Claim 13 is the slit lamp microscope according to Claim 1 or Claim 8, wherein in the correspondence information, the standard setting conditions regarding light sensitivity of the image sensor are associated with each of the multiple sites, and the acquiring part acquires the current setting states regarding the light sensitivity.

An invention described in Claim 14 is the slit lamp microscope according to Claim 1 or Claim 8, wherein in the correspondence information, the standard setting conditions regarding electric charge accumulation time of the image sensor are associated with each of the multiple sites, and the acquiring part acquires the current setting states regarding the electric charge accumulation time.

An invention described in Claim 15 is the slit lamp microscope according to Claim 1 or Claim 8, wherein the direction of the optical axis of the observation system can be changed, in the correspondence information, the standard setting conditions regarding the direction of the optical axis are associated with each of the multiple sites, and the acquiring part acquires the current setting states regarding the direction of the optical axis.

Effect of the Invention

According to the slit lamp microscope related to the present invention is capable of specifying a part of the device in which its current setting state is different from the standard setting condition corresponding to the designated site of the eye, and displaying this. Therefore, it is possible to appropriately and easily carry out the setting of the optical system of the device.

BRIEF DESCRIPTION OF THE DRAWINGS

FIG. 3 is a schematic block diagram illustrating an example of a configuration of the control system of an embodiment of a slit lamp microscope according to the present invention.

FIG. 4 is a schematic diagram illustrating an example of standard-setting-condition information of an embodiment of a slit lamp microscope according to the present invention.

FIG. 6 is a schematic diagram illustrating an example of a display mode of information in an embodiment of a slit lamp microscope according to the present invention.

MODE FOR CARRYING OUT THE INVENTION

Figure 1:
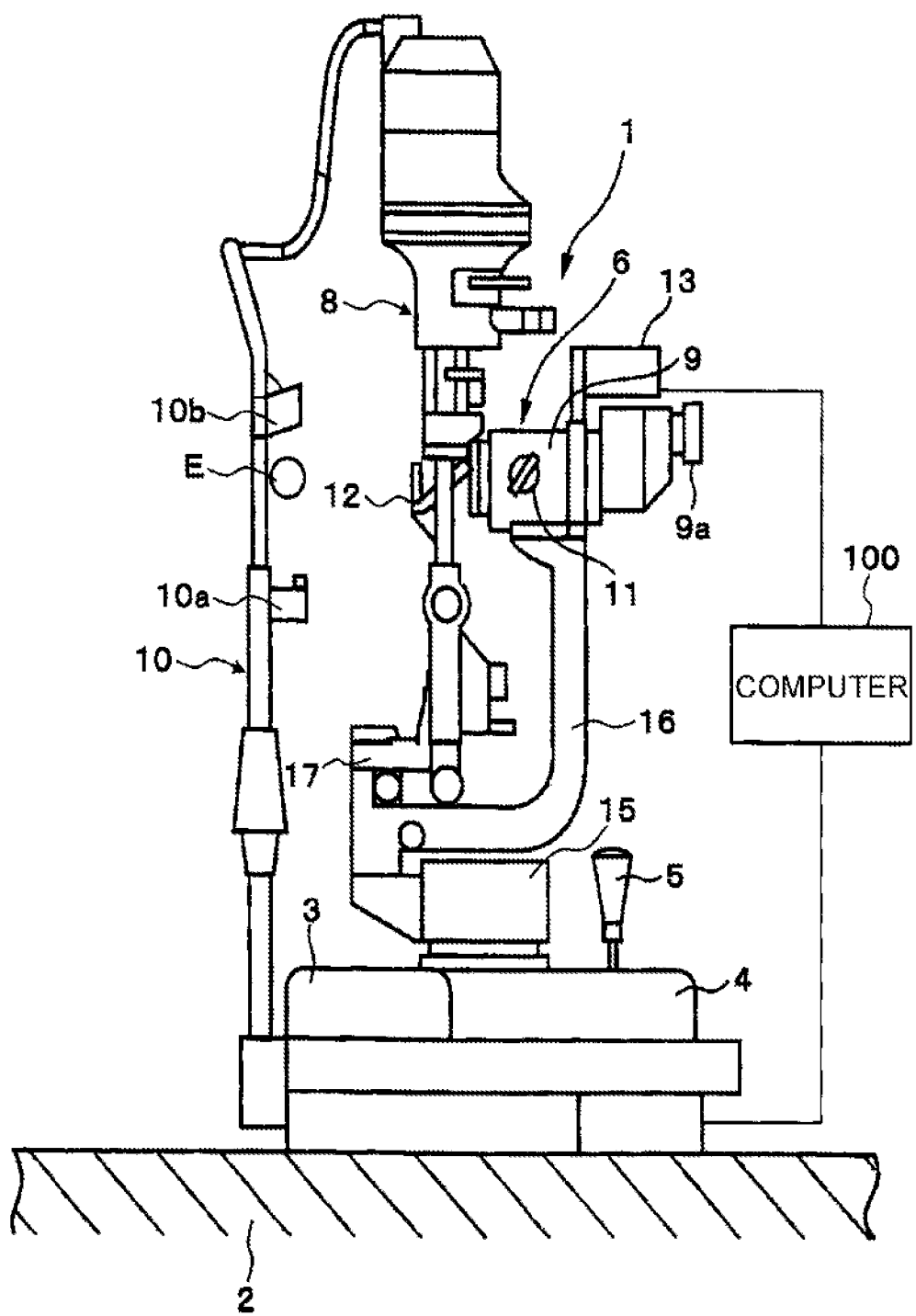
FIG. 1 is a schematic side view illustrating an example of the exterior configuration of an embodiment of a slit lamp microscope according to the present invention.

Examples of embodiments of a slit lamp microscope related to the present invention are explained in detail with reference to the diagrams.

First, the directions are defined. The direction from a lens (objective lens) positioned closest to the subject side in a device optical system is a "front direction", while the direction opposite from this is "rear direction". Moreover, the horizontal direction orthogonal to the front direction is a "left-right direction". Further, the direction orthogonal to both the front-rear direction and the left-right direction is an "upward-downward direction".

[Exterior Configuration]

The exterior configuration of the slit lamp microscope related to the present embodiment is explained with reference to FIG. 1. A computer 100 is connected to the slit lamp microscope 1. The computer 100 carries out various control processes and arithmetic processes. It should be noted that, rather than providing a computer 100 separate from a main body of the microscope (a case for housing an optical system, etc.), a configuration can be applied in which a similar computer is arranged within the main body of the microscope.

The slit lamp microscope 1 is placed on a table 2. It should be noted that the computer 100 may be arranged on the other table or other locations. A base 4 is configured to be movable in the horizontal direction via a moving mechanism 3. The base 4 moves by the tilting operation of an operation handle 5.

The top surface of the base 4 is provided with a supporting part 15 that supports an observation system 6 and an illumination system 8. A supporting arm 16 for supporting the observation system 6 is provided on the supporting part 15 such that it is capable of rotating in the left-right direction. A supporting arm 17 supporting the illumination system 8 is provided on the top part of the supporting arm 16 such that it is capable of rotating in the left-right direction. The supporting arms 16 and 17 are independently turnable around the same axis. The direction of the optical axis of the observation system 6 can be changed (that is, the observation direction can be changed) by turning the supporting arm 16. Further, the direction of the optical axis of the illumination system 8 can be changed (that is, the illumination direction can be changed) by turning the supporting arm 17.

The respective supporting arms 16 and 17 may be configured so as to be turned by an electric mechanism, or so as to be turned manually. In the former case, the followings are provided: an actuator generating a driving force for turning the supporting arms 16 (or the supporting arms 17); and a transmission mechanism transmitting this driving force to turn the supporting arms 16 (or the supporting arms 17). The actuator is configured by, for example, a stepping motor (a pulse motor). The transmission mechanism is configured by, for example, a combination of gearwheels, or rack and pinion, etc.

The illumination system 8 may be configured such that it is allowed to be swung in the upward-downward direction. That is, it may be configured such that the angle of elevation and the angle of depression of the illumination light can be changed. The mechanism that turns the illumination system 8 is driven electrically or manually in the same way as that for the observation system 6. This is the same for the observation system 6.

The observation system 6 comprises a left-and-right pair of optical systems for guiding returned light of the illumination light from the eye E. These optical systems are housed within a lens tube body 9. The end of the lens tube body 9 is an eyepiece 9a. The user observes the eye E by looking into the eyepiece 9a with the naked eyes.

It should be noted that the returned light of the illumination light includes a variety of lights having traveled the eye E such as scattered light, and these variety of lights are collectively referred to as "returned light." Further, a light source (a background light source 70 illustrated in FIG. 2) that outputs background light is provided in the peripheral position.

A jaw holding platform 10 is arranged in a position facing the lens tube body 9. The jaw holding platform 10 is provided with a jaw holder 10a and a forehead supporter 10b for stably placing the subject face.

An observation magnification operating knob 11 for changing the observation magnification is arranged on the side surface of the lens tube body 9. The observation magnification may be changed by an electrical mechanism. Further, an imaging device 13 for imaging the eye E is connected to the lens tube body 9. The imaging device 13 comprises an image sensor. The image sensor is a photoelectric transducer that detects light and outputs electric signals (image signals). The image signals are input into the computer 100. For the image sensor, for example, a CCD (Charge Coupled Device) image sensor or a CMOS (Complementary Metal Oxide Semiconductor) image sensor is used. A mirror 12 for reflecting illumination light beam output from the illumination system 8 towards the eye E is arranged in a lower position of the illumination system 8.

Figure 2:
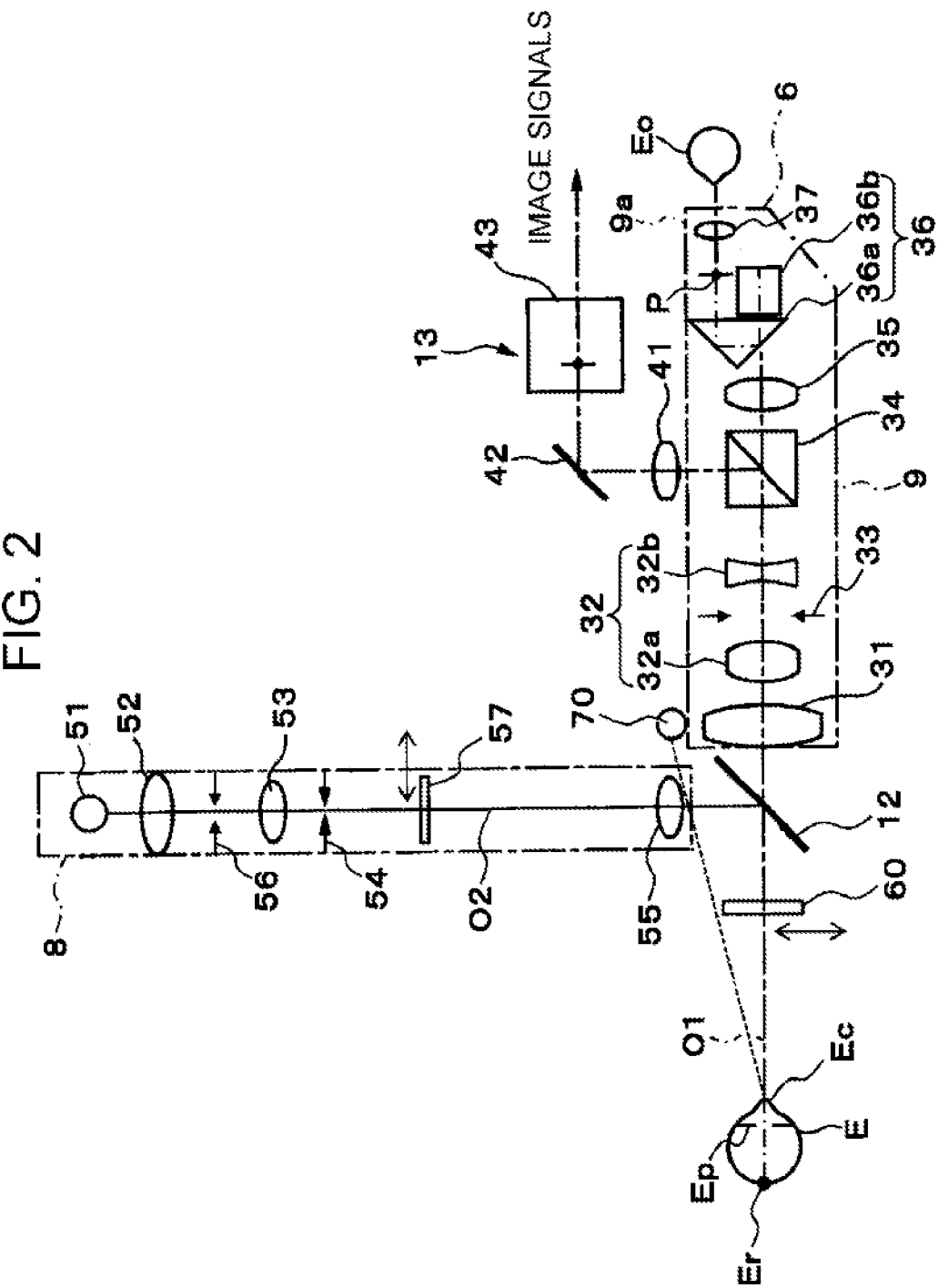
FIG. 2 is a schematic side view illustrating an example of a configuration of the optical system of an embodiment of a slit lamp microscope according to the present invention.

Moreover, although omitted in FIG. 1, a diffused plate 60 illustrated in FIG. 2 is inserted/removed with respect to the front position of mirror 12. The diffused plate 60 diffuses the illumination light, thereby uniformly irradiating the illumination light with respect to eye E, the diffused plate 60 may be an optical member having only a diffusing function or may be an optical member having both a diffusing function as well as a lens function. The diffused plate 60 is an example of a "diffusion member."

[Configuration of the Optical System]

The configuration of the optical system of the slit lamp microscope 1 is described with reference to FIG. 2. The slit lamp microscope 1 comprises the observation system 6 and the illumination system 8.

[Observation System]

The observation system 6 comprises a left-and-right pair of optical systems. The left and right optical systems have substantially the same configuration. By means of these left and right optical systems, the user is capable of observing the eye E with both eyes. It should be noted that FIG. 2 illustrates only one of the left and right optical systems of the observation system 6. The symbol O1 is the optical axis (observation optical axis) of the observation system 6. The change of the observation direction with respect to the eye E (described above) corresponds to the change of the angle (observation angle) with respect to a predetermined standard position of the observation optical axis O1.

Each of the left and right optical systems of the observation system 6 comprises an objective lens 31, magnification optical system 32, diaphragm 33, relay lens 35, prism 36, and eyepiece lens 37. The beam splitter 34 is provided to only one or both of the left and right optical systems. The eyepiece lens 37 is provided inside the eyepiece 9a. The symbol P indicates the imaging position of the light guided towards the eyepiece lens 37. The symbol Ec indicates the cornea of the eye E, the symbol Ep indicates the iris, and the symbol Er indicates the fundus, respectively. The symbol Eo indicates a tester's eye.

The magnification optical system 32 comprises a plurality (for example, two) of magnifying lens 32a and 32b. The respective magnifying lens 32a and 32b is configured so as to be movable along the observation optical axis O1. Thereby, the magnification (angle of view) of observation images as well as photographed images of the eye E may be changed. The change of the magnification is carried out by operating the observation magnification operating knob 11. Moreover, a configuration is possible in which the magnification is electrically changed using a switch (not illustrated) etc.

The beam splitter 34 divides the light travelling along the observation optical axis O1 into two. The light that has penetrated the beam splitter 34 is guided to the user's eye Eo via the prism 36, and the eyepiece lens 37. The prism 36 comprises two optical elements 36a and 36b, and parallelly displaces the travelling direction of the light upwards.

Meanwhile, the light that has been reflected by the beam splitter 34 is guided to the image sensor 43 of the imaging device 13 via the relay lens 41 and the mirror 42. The image sensor 43 detects this reflected light to generate image signals.

[Illumination System]

The illumination system 8 comprises a light source 51, relay lens 52, illumination diaphragm 56, condensing lens 53, slit forming part 54, filter 57, condensing lens 55, and diffused plate 60. The symbol O2 indicates the optical axis (illumination optical axis) of the illumination system 8. The change of the illumination direction with respect to the eye E (described above) corresponds to the change of the angle (illuminating angle) with respect to a predetermined standard position of the illumination optical axis O2.

The light source 51 outputs illumination light. It should be noted that a plurality of light sources may be provided in the illumination system 8. For example, both a light source outputting a continuous light (halogen lamp, LED, etc.) and a light source outputting a flash light (xenon lamp, LED, etc.) may be provided as the light source 51. Moreover, a light source for cornea observation and a light source for fundus observation may be separately provided.

The slit forming part 54 forms a slit in order to generate slit light. The slit forming part 54 comprises a pair of slit blades. By changing the interval of these slit blades, the slit width is changed. The slit width when the interval of the slit blades is maximal may be equal to or greater than the beam diameter of the illumination light. The illumination light in this case is also referred to as a slit light, as a matter of convenience.

The illumination diaphragm 56 blocks off the periphery part of the illumination light, and transmits only the central region thereof. The illumination diaphragm 56 may be configured such that the size of the light-transmitting part thereof may be changed (that is, it may be configured such that the diaphragm value may be changed). The illumination diaphragm 56 is used for reducing reflection of the illumination light by the cornea Ec and/or crystalline lens and for adjusting the brightness of the illumination light.

The filter 57 is generally an optical element having an effect of removing or weakening a particular component of the illumination light. The filter 57 is, for example, a blue filter (filter that specifically transmits a wavelength component corresponding to blue color). The filter 57 is capable of inserting into and removed from the light path of the illumination light.

The diffused plate 60 diffuses the illumination light as described above. The diffused plate 60 is capable of inserting into and removed from the light path of the illumination light.

[Configuration of Control System]

The control system of the slit lamp microscope 1 is explained with reference to FIG. 3. The control system of the slit lamp microscope 1 is configured with a controller 101 as the center. It should be noted that FIG. 3 illustrates only the particularly focal components in this embodiment, with other components omitted.

[Controller]

The controller 101 controls each part of the slit lamp microscope 1. For example, the controller 101 carries out control of the observation system 6, control of the illumination system 8, etc.

The control of the observation system 6 includes control of the diaphragm 33, control of the image sensor 43, etc. Control of the image sensor 43 includes control of electric charge accumulation time, control of light sensitivity, control of frame rate, etc. the controller 101 controls a power-varying mechanism 132 to change the magnification by the magnification optical system 32. The controller 101 controls an observation system turning mechanism 106 to horizontally turn the observation system 6 with the support arm 16 as the axis. It should be noted that the observation system turning mechanism 106 may be configured such that the observation system 6 vertically turns due to control by the controller 101. The power-varying mechanism 132 and the observation system turning mechanism 106 are respectively configured by comprising an actuator and a transmission mechanism.

The control of the illumination system 8 includes control of the light source 51, control of the slit forming part 54, etc. The controller 101 controls a diaphragm driving mechanism 156 to change the diaphragm value of the illumination diaphragm 56. The controller 101 controls a filter driving mechanism 157 to insert/remove the filter 57 into/from the light path. The controller 101 controls a diffused plate driving mechanism 160 to insert/remove the filter 57 into/from the light path. The controller 101 controls an illumination system turning mechanism 108 to horizontally turn the illumination system 8 with the support arm 17 as the axis. The illumination system turning mechanism 108 may be configured such that the illumination system 8 vertically moves due to control of the controller 101. The slit forming part 54, the diaphragm driving mechanism 156, the filter driving mechanism 157, the diffused plate driving mechanism 160, and the illumination system turning mechanism 108 are respectively configured by comprising an actuator and a transmission mechanism.

The controller 101 controls the moving mechanism 3 to horizontally move the observation system 6 and the illumination system 8. The moving mechanism 3 is an example of the "moving mechanism."

The controller 101 controls the background light source 70 to output the background light.

The controller 101 carries out a process of reading data stored in the storage 102 and a process of writing data into the storage 102.

The controller 101 comprises a microprocessor, RAM. ROM, hard disk drive, etc. Control programs are stored in advance in this hard disk drive. Operations of the controller 101 are realized by cooperation of the control programs and the aforementioned hardware.

The controller 101 is arranged in the main body (for example, in the base 4) of the slit lamp microscope 1 and/or the computer 100.

[Storage]

The storage 102 stores various types of data and computer programs. The storage 102 comprises storage devices such as a RAM, ROM, hard disk drive, etc.

The storage 102 stores standard-setting-condition information 110. In the standard-setting-condition information 110, standard setting conditions of the observation system 6 and/or the illumination system 8 are associated with each of a plurality of sites of an eye. The standard setting conditions refer to setting conditions of the optical system when observing a certain site of an eye: in other words, it indicates operating states of members included in the observation system 6 and/or the illumination system 8 applied when observing a specific site of an eye. The standard-setting-condition information 110 is an example of the "correspondence information."

The standard-setting-condition information 110 is stored in the storage 102 prior to examination. It should be noted that the standard-setting-condition information 110 may be, for example, default information stored at shipment or delivery of the device or may be that made for each user. Moreover, users, etc. are capable of appropriately changing the standard-setting-condition information 110.

An example of the standard-setting-condition information 110 is illustrated in FIG. 4. The standard-setting-condition information 110 illustrated in FIG. 4 is provided with the following items: "site;" "observation technique;" "magnification;" "slit width;" "amount of light;" "illuminating angle;" "background illumination;" "diffused plate;" and "filter." Among the site items, the following are listed as the sites of an eye that are subject to observation: "anterior segment;" "conjunctiva;" "cornea;" "iris;" "crystalline lens;" "corner angle;" "vitreous body;" and "retina."

The column for the anterior segment is associated with the following as the standard setting conditions: the observation technique "diffused illumination;" the magnification "16;" the slit width "fully opened;" the amount of light "3 to 4;" the illuminating angle "10 to 30°;" the background illumination "absent;" the diffused plate "present;" and filter "absent." It should be noted that the amount of light is expressed by 5 levels (1 to 5: larger numbers have greater amount of light). The illuminating angle is expressed as the horizontal angle of the illumination optical axis O2 with respect to the vertical plane (plane extending in the vertical direction and the front-rear direction) including the observation optical axis O1. It should be noted that the direction of the illuminating angle with respect to this vertical plane (angle to the left or angle to the right) depends on whether the eye E is a left eye or a right eye; therefore, it is not taken into account in the standard-setting-condition information 110.

The columns for other sites are similar to the column for the anterior segment. It should be noted that the column for the cornea and the column for the crystalline lens are associated with two or more observation techniques. Also, with respect to each combination of site and observation technique, standard setting conditions such as magnification, etc. are associated.

The item diffused plate in the iris column is "present/absent," indicating that the diffused plate 60 is used when observing wide areas and not for other cases. It should be noted that whether the observation range is wide or not is determined according to, for example, the observation magnification. Specifically, it is determined as a wide range observation if the observation magnification is equal to or less than a predetermined threshold, and determined as a narrow range observation in other cases.

[Display]

The display 103 is controlled by the controller 101 to display a variety of information. The display 103 comprises any kinds of display device, for example, a flat panel display such as LCD, etc., or a CRT display. The display 103 may be provided in the main body of the slit lamp microscope 1 or in the computer 100.

[Operation Part]

The operation part 104 comprises an operation device and/or an input device. The operation part 104 comprises buttons and switches provided in the main body (for example, the operation handle 5, etc.) and a mouse, keyboard, etc. of the computer 100. Moreover, it is possible to use any operation devices and input devices such as a trackball, dedicated operation panel, switch, button, dial, etc.

In FIG. 3, the display 103 and the operating part 104 are separately illustrated: however, these may be integrally configured. As a detailed example thereof, a touch panel LCD may be used.

[Data Processor]

A data processor 120 carries out a variety of data processing. The data processor 120 is provided with a searching part 121, a setting-state acquiring part 122, and a setting-state specifying part 123.

(Searching Part)

The searching part 121 searches the standard setting conditions corresponding to a site of the eye E designated by the user. For example, if "cornea" is designated by the user, four sets of the standard setting conditions corresponding to the cornea are searched from the standard-setting-condition information 110.

(Setting-state Acquiring Part)

The setting-state acquiring part 122 acquires the current setting states of the illumination system 8 and/or the observation system 6. The setting-state specifying part 123 is an example of the "acquiring part."

In the present embodiment, each part of the optical system is controlled by the controller 101 therefore, the controller 101 recognizes and stores the control content with respect to the each part. Accordingly, the setting-state acquiring part 122 can acquire the current setting state of each part from the controller 101. It should be noted that the control items inquired from the setting-state acquiring part 122 to the controller 101 may only be the items included in the standard-setting-condition information 110 (in this embodiment, the value of the magnification, the value of the slit width, the value of the amount of light, the value of the illuminating angle, the presence or absence of the background illumination (and its amount of light), the presence or absence of the diffused plate 50, and the presence or absence of the filter 57).

Another example of the setting-state acquiring part 122 is explained. In the example mentioned above, all current setting states are acquired from the controller 101; however, a configuration is possible for detecting at least from among these settings by the sensor. This configuration is particularly effective when manually changing the setting states. For example, when manually changing the magnification using the observation magnification operating knob 11, a sensor (potentiometer, etc.) for detecting the rotational position of the observation magnification operating knob 11 or the positions of the variable-power lens 32a and 32b may be provided and the current magnification value may be acquired based on the output from this sensor. The slit width value, the value of the amount of light, the value of the illuminating angle, the presence or absence of the background illumination, the presence or absence of the diffused plate 60, and the presence or absence of the filter 57 may also be acquired by respectively using an appropriate sensor (potentiometer, photodiode, infrared radiation sensor, etc.).

(Setting-state Specifying Part)

The setting-state specifying part 123 specifies, from among the current setting states acquired by the setting-state acquiring part 122, those differing from the standard setting conditions searched by the searching part 121. The setting-state specifying part 123 is an example of the "specifying part."

It should be noted that when multiple sets of the standard setting conditions are searched, that is, when there are multiple observation techniques corresponding to the observation target site designated by the user, for example, one from among the following two processes is carried out by the setting-state specifying part 123. As the first process, the setting-state specifying part 123 respectively carries out concerned processes with respect to the standard setting conditions of the multiple observation techniques searched by the searching part 121. As the second process, when the observation technique is designated, the setting-state specifying part 123 carries out concerned processes only with respect to this designated observation technique.

An example of processes carried out by the setting-state specifying part 123 is explained. When "cornea" is designated as the observation target site, the searching part 121 acquires the four sets of the standard setting conditions in which the item "site" is the "cornea," that is, it acquires the four sets of the standard setting conditions in which "observation technique" corresponds to "diffused illumination," "direct illumination," "background illumination," "fluorescent staining" as the searching result. Moreover, the setting-state acquiring part 122 acquires the current setting states regarding each of the following items: "magnification;" "slit width;" "amount of light;" "illuminating angle;" "background illumination;" "diffused plate;" and "filter."

When the first process mentioned above is applied, for each of the searched four sets of the standard setting conditions, the setting-state specifying part 123 compares the value (including the state) recorded in each item with the current setting state acquired for the concerned item, and determines whether or not they coincide with each other. It should be noted that if the former indicates a range (for example, the amount of light "3 to 4", etc.), it is determined whether the latter is included in the former. Thereby, the setting-state specifying part 123 specifies those in which the value recorded in the standard-setting-condition information 110 differs from the current setting states for each item in each set of the standard setting conditions.

When the second process mentioned above is applied, the user designates a desired observation technique using the operation part 104. Alternatively, a configuration is possible in which the observation technique is specified from the electric medical record of the subject and then designated. Moreover, a configuration is also possible in which the observation technique is specified based on the current setting states acquired by the setting-state acquiring part 122 and then designated (for example, it may be configured such that the observation technique that best conforms to the current setting states is selected). Moreover, in the event of carrying out a plurality of examinations in a predetermined order, a configuration is possible of specifying and designating the observation technique corresponding to the following examination based on this order.

Once the observation technique is designated, for the standard setting conditions of each item corresponding to this designated observation technique, the setting-state specifying part 123 compares the value (including the state) recorded in each item with the current setting state acquired for the concerned item, and determines whether or not they conform to each other. Thereby, regarding each item of the designated observation technique, those in which the value recorded in the standard-setting-condition information 110 differs from the current setting states are specified.

[Operation]

The operations of the slit lamp microscope 1 are explained.

(1st Operation Example)

Figure 5:
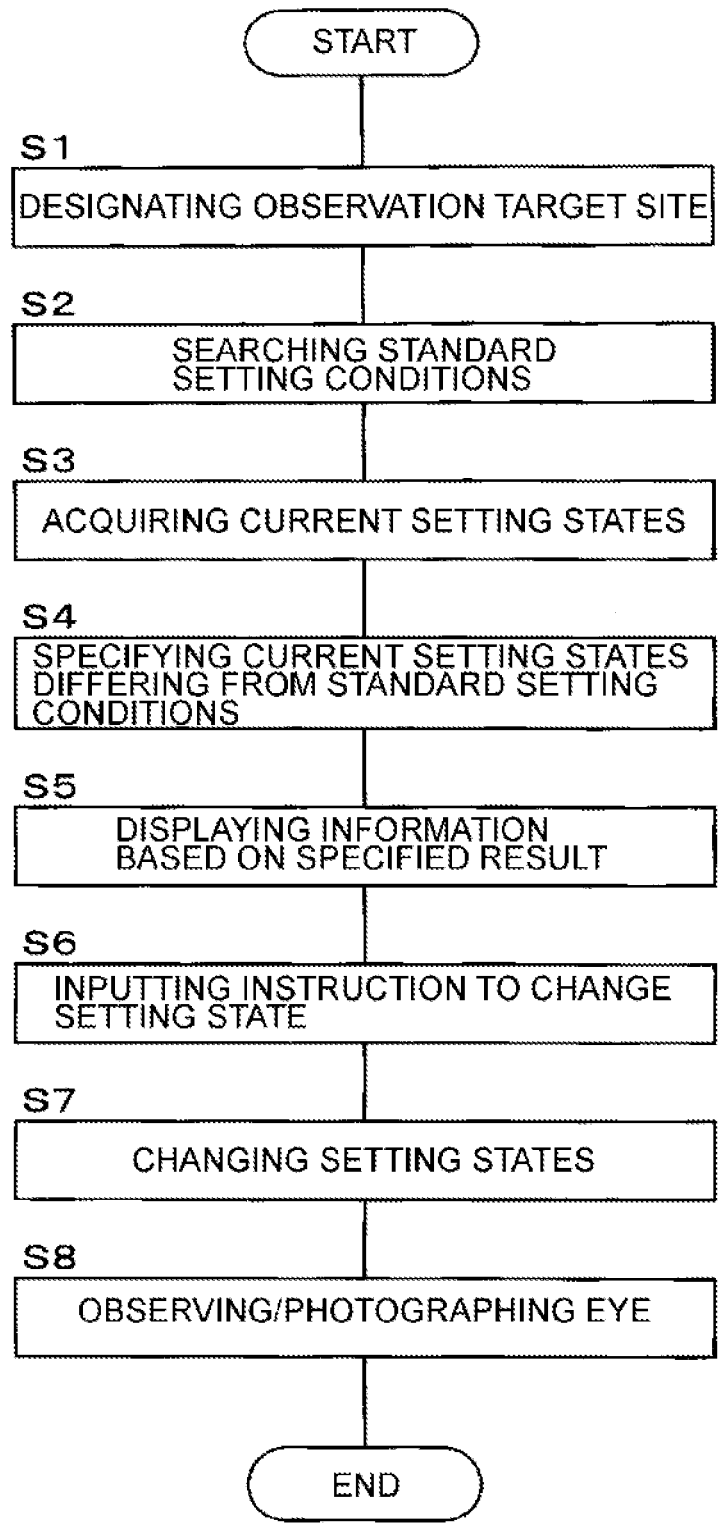
FIG. 5 is a flow chart illustrating an example of an operation of an embodiment of a slit lamp microscope according to the present invention.

An first example of the operation of the slit lamp microscope 1 is illustrated in FIG. 5.

(Step 1)

A tester designates an observation target site of the eye E. This operation is carried out by, for example, selecting the desired observation target site from a list presented on the display screen using the operation part 104.

(Step 2)

The searching part 121 searches the standard setting conditions corresponding to the designated observation target site in Step 1 from the standard-setting-condition information 110.

(Step 3)

The setting-state acquiring part 122 acquires the current setting states regarding each of: the value of the observation magnification; the value of the slit width; the value of the amount of light of the illumination light, the value of the irradiation angle of the illumination light, the presence or absence of the background illumination light, the presence or absence of the diffused plate 60 in the illumination light path, and the presence or absence of the filter 57 in the illumination light path.

(Step 4)

The setting-state specifying part 123 specifies from among the current setting states acquired in Step 3, those differing from the standard settings searched in Step 2.

(Step 5)

The controller 101 displays information based on the specified result in Step 4 on the display 103. This displayed information presents, for example, the current setting states specified in Step 4 in a manner differing from the current setting states conforming to the standard setting conditions. A display example in the event the cornea is designated as the observation target site is illustrated in FIG. 6.

The controller 101 displays a setting operation screen 170 illustrated in FIG. 6 on the display 103. The setting operation screen 170 is provided with an observation-target-site displaying part 171, a setting-content displaying part 172, and a setting-changing button 173.

The designated observation target site is displayed on the observation-target-site displaying part 171 in Step 1. In this example, the text string "Cornea" is displayed.

Information based on the specified result in Step 4 is displayed on the setting-content displaying part 172. In this example, from among the respective standard setting conditions of the four observation techniques of the cornea, those determined to be different from the current setting states in Step 4 are displayed. That is, only the standard setting conditions differing from the current setting states are displayed, while the standard setting conditions conforming to the current setting states are not displayed. Moreover, the current setting states are also displayed on the setting-content displaying part 172.

The tester may designate the desired observation technique from among those exhibited in the setting-content displaying part 172 using the operation part 104. This operation involves, for example, a clicking operation using a mouse. As an example of the process corresponding to the designation of an observation technique, the controller 101 deletes the displayed information related to the observation techniques that have not been designated. Thereby, only the information regarding the designated observation technique is displayed. Moreover, a configuration is possible of presenting the information regarding the designated observation technique in a manner differing from other information (color, hatching, enclosure, etc.). Moreover, it is preferably configured such that, even when the observation technique has been designated at one point, another observation technique may be designated again. A pull-down menu may be an example thereof.

A configuration is possible in which the contents displayed on the setting-content displaying part 172 are changed. As an example thereof, a configuration is possible in which the operation part 104 is operated such that the desired settings may be input. This input operation may be carried out using, for example, a keyboard. Moreover, a configuration is possible in which a software key for inputting information is displayed on the display 103 and this software key is operated using the operation part 103 (mouse, etc.), thereby carrying out this input operation. Moreover, the display region of each standard setting condition may be configured as a pull-down menu.

It is convenient if the operation for changing the observation target site may be carried out on the setting operation screen 170. As a configuration example for this purpose, the observation-target-site displaying part 171 may be a pull-down menu. When a new observation target site is designated, the controller 101 carries out the abovementioned process again to update the contents displayed on the setting-content displaying part 172.

The setting-changing button 173 is an example of an operation key for inputting an instruction for changing the specified current setting states in Step 4. When a plurality of observation techniques is presented, the tester specifies a desired observation technique. Further, the tester arbitrarily changes the presented standard setting conditions as needed.

(Step 6)

Following the operation mentioned above, the tester operates the setting-changing button 173 using the operation part 104 (for example, a clicking operation using a mouse is carried out).

(Step 7)

The controller 101 that received this operation controls respective parts of the device based on the standard setting conditions (if having been changed, the setting conditions after the change), thereby changing the setting of respective parts of the device to conform this to the concerned standard setting condition.

As a specific example, if "diffused illumination" is selected on the setting operation screen 170 in FIG. 6, the controller 101 controls the power-varying mechanism 132 to change the magnification from "25 fold" to "16 fold" along with controlling the light source 51 to change the amount of illumination light from "1" to, for example, "3." It should be noted that, regarding the automatic setting of the amount of illumination light, in order to reduce the risk of the subject feeling brightness, the minimum value of the amount of light is preferably selected from within the range indicated in the standard setting conditions.

(Step 8)

Following the above-mentioned preparations, the tester operates the operation part 104 to commence observation (including photographing) of the eye E.

(2nd Operation Example)

An explanation is provided regarding the operation of the slit lamp microscope 1, taking into consideration whether eye E is the left or right eye.

As mentioned above, the moving mechanism 3 horizontally moves the optical system of the device. If eye E is a left eye, the optical system of the device is moved to the right side, while if it is a right eye, it is moved to the left side. Accordingly, it is possible to determine whether the eye E is a left eye or a right eye based on the setting state of the moving mechanism.

It should be noted that when a configuration is applied in which the controller 101 controls the moving mechanism 3, the controller 101 may recognize the current setting state of the moving mechanism 3. Meanwhile, when a configuration is applied in which the user manually operates the moving mechanism 3, a sensor for detecting the current setting state of the moving mechanism 3 (position sensor, etc.) is used.

Hereinafter, an explanation is provided regarding the operation example controlling the illuminating angle in accordance with whether eye E is a left eye or a right eye with reference to the flow chart of the 1st operation example (FIG. 5). It should be noted that a similar control may be appropriately carried out regarding the subject for controls other than the illuminating angle.

When the observation target site of the eye E is designated by the tester (S1), the searching part 121 searches the standard setting conditions corresponding to the designated site (S2).

The setting-state acquiring part 122 acquires the current setting states of each part of the device (S3). At this time, the current setting state of the moving mechanism 3, that is, information corresponding to the current horizontal position of the optical system of the device is acquired. An example of this information includes the horizontal position of the turning axis (the support arms 16, 17) of the observation system 6 and the illumination system 8.

Subsequently, the setting-state specifying part 123 specifies the current setting states differing from the standard setting conditions (S4). Here, it is not particularly necessary to carry out comparison processing with the standard setting conditions regarding the current setting state of the moving mechanism 3. The controller 101 displays information based on the specified result at S4 (for example, the setting operation screen 170) on the display 103 (S5).

When the tester inputs an instruction to change the setting state (S6), the controller 101 changes the setting state of respective parts of the device (S7).

In the event the illuminating angle is changed in S7, the current setting state of the moving mechanism 3 acquired in S3 is taken into consideration. As an example thereof, the controller 101 gradually changes the illuminating angle to the targeted setting state in correspondence with whether or not the eye E is a left eye or a right eye, that is, whether the optical system of the device is located on the right side or the left side.

At this time, the illuminating angle is preferably changed in the direction in which the angle of the illumination optical axis O2 increases with respect to the observation optical axis O1. In order to do this, the current setting state of the observation system turning mechanism 106 is acquired in S3 and the current direction of the observation optical axis O1 is recognized. Subsequently, in S7, controller 101 gradually increases the illuminating angle with respect to the observation optical axis O1 based on the current setting state of the moving mechanism 3, the current direction of the observation optical axis O1, the current illuminating angle, and the illuminating angle indicated in the standard setting conditions, thereby realizing the illuminating angle indicated in the standard setting conditions.

It should be noted that, as an operation example in which the current illuminating angle with respect to the observation optical axis O1 is larger than the angle indicated in the standard setting conditions, a configuration is possible of first aligning the illuminating angle with the observation optical axis O1 (or vicinity thereof) and then gradually changing it to the intended angle. In the step of aligning the illuminating angle with the observation optical axis O1, the light source 51 may be turned on or off.

(3rd Operation Example)

An explanation is provided regarding the operation of the slit lamp microscope 1 in the event the setting state of the illumination diaphragm 56 is changed.

The current setting state of the illumination diaphragm 56 may be acquired based on the content of control of the diaphragm driving mechanism 156 by the controller 101. Meanwhile, when manually changing the diaphragm value of the illumination diaphragm 56, a sensor for detecting information corresponding to this diaphragm value is provided. Regarding this sensor, a position sensor (for example, a potentiometer for detecting the rotational state of the knob) for detecting the operation content for changing this diaphragm value may be used. Moreover, a configuration is possible of detecting the beam diameter of the illumination light that has passed through the illumination diaphragm 56, thereby acquiring the diaphragm value.

Hereinafter, an explanation is provided regarding an operation example for controlling the diaphragm value of the illumination diaphragm 56 with reference to the flow chart of the 1st operation example (FIG. 5).

When the observation target site of the eye E is specified by the tester (S1), the searching part 121 searches the standard setting conditions corresponding to the designated site (S2). Here, when the standard setting condition of the diaphragm value of the illumination diaphragm 56 is included in the standard-setting-condition information 110, this is also searched. It should be noted that this diaphragm value is related to the amount of light of the illumination light. That is, if the amount of light is great (small), the diaphragm value is also great (small). The standard-setting-condition information 110 may record one value of the amount of light and one value of the diaphragm value, or may record a range of the amount of light and a range of the diaphragm value by associating them with each other.

The setting-state acquiring part 122 acquires the current setting states of each part of the device (S3). At this time, the current setting state of the illumination diaphragm 56, that is, information corresponding to the current diaphragm value of illumination diaphragm 56 is acquired.

Subsequently, the setting-state specifying part 123 specifies the current setting states differing from the standard setting conditions (S4). It should be noted that if the standard setting condition of the diaphragm value of the illumination diaphragm 56 is searched in S2, comparison processing is carried out between this standard setting condition and the current diaphragm value. Meanwhile, in the event the standard setting condition of the diaphragm value of the illumination diaphragm 56 is not searched in S2, there is no need to carry out comparison processing regarding the diaphragm value. The controller 101 displays information based on the specified result in S4 (for example, the setting operation screen 170) on the display 103 (S5).

When the tester inputs instructions for changing the setting states (S6), the controller 101 changes the setting of respective parts of the device (S7). At this time, the controller 101 changes the diaphragm value of the illumination diaphragm 56. This control gradually decreases the diaphragm value from, for example, a state of a large diaphragm value (including a state in which the illumination diaphragm 56 is closed) with a fixed amount of light. Alternatively, this control may gradually increase the amount of light from a state of a small amount of light (including a state with the light off) with a fixed diaphragm value. Moreover, it is also possible to synchronously control the amount of light and the diaphragm value, thereby controlling such that the amount of light irradiated onto the eye E (that is, the amount of illumination light passing the illumination diaphragm 56) gradually increases.

(4th Operation Example)

Hereinafter, an explanation is provided regarding the operation of the slit lamp microscope 1 in the event of changing the setting state on the light sensitivity of the image sensor 43.

Image sensor 43 is controlled by the controller 101. Accordingly, the controller 101 recognizes the current setting state of the light sensitivity of the image sensor 43. It should be noted that when the light sensitivity of the image sensor 43 is manually set by the user, a configuration is possible such that signals indicating the setting state thereof are transmitted from the image sensor 43 to the controller 101.

Hereinafter, an explanation is provided regarding the operation example for controlling the light sensitivity of the image sensor 43 with reference to the flow chart of the 1st operation example (FIG. 5).

When the observation target site of the eye E is specified by the tester (S1), the searching part 121 searches the standard setting conditions corresponding to the designated site (S2). Here, when the standard setting condition of the light sensitivity of the image sensor 43 is included in the standard-setting-condition information 110, this is also searched. It should be noted that this light sensitivity is related to the amount of the illumination light. That is, the maximum amount of the illumination light to be irradiated on an eye is determined in advance from the viewpoint of safety, and the light sensitivity is set based on this maximum amount of light. Moreover, in order to achieve a reduction in noise, low light sensitivity is preferably used as much as possible. The standard setting condition of the light sensitivity recorded in the standard-setting-condition information 110 is determined taking these conditions into consideration. The standard-setting-condition information 110 may record one value of amount of light and one value of the light sensitivity, or may record a range of the amount of light and a range of the light sensitivity by associating them with each other.

The setting-state acquiring part 122 acquires the current setting states of respective parts of the device (S3). At this time, the current setting state of the light sensitivity of image sensor 43 is acquired.

Subsequently, the setting-state specifying part 123 specifies the current setting states differing from the standard setting conditions (S4). It should be noted that when the standard setting condition of the light sensitivity of the image sensor 43 is searched in S2, comparison processing is carried out between this standard setting condition and the current light sensitivity. Meanwhile, if the standard setting condition of the light sensitivity of the image sensor 43 is not searched in S2, there is no need to carry out comparison processing regarding the light sensitivity. The controller 101 displays information based on the specified result in S4 (for example, the setting operation screen 170) on the display 103 (S5).

When the tester inputs an instruction for changing the setting states (S6), the controller 101 changes the setting states of respective parts of the device (S7). At this time, the controller 101 changes the light sensitivity of the image sensor 43.

(5th Operation Example)

An explanation is provided regarding the operation of the slit lamp microscope 1 in the event the setting state of the electric charge accumulation time of the image sensor 43 is changed.

The image sensor 43 is controlled by the controller 101. Accordingly, the controller 101 recognizes the current setting state of the electric charge accumulation time of the image sensor 43. It should be noted that a configuration is possible in which, when the user manually sets the electric charge accumulation time of the image sensor 43, signals indicating the setting state thereof are transmitted from the image sensor 43 to the controller 101.

Hereinafter, the operation example for controlling the electric charge accumulation time of the image sensor 43 is explained with reference to the flow chart (FIG. 5) of the 1st operation example.

When the observation target site of the eye E is specified by the tester (S1), the searching part 121 searches the standard setting conditions corresponding to the designated site (S2). Here, when the standard setting condition of the electric charge accumulation time of the image sensor 43 is included in the standard-setting-condition information 110, this is also searched. It should be noted that this electric charge accumulation time is related to the amount of the illumination light, light-emitting time (when photographing with flash light) of the illumination light, the light sensitivity, etc. That is, the electric charge accumulation time is a factor in determining the exposure along with these conditions. The standard setting condition of the electric charge accumulation time recorded in the standard-setting-condition information 110 is determined taking these conditions into consideration.

The setting-state acquiring part 122 acquires the current setting states of respective parts of the device (S3). At this time, the current setting state of the electric charge accumulation time of the image sensor 43 is acquired.

Subsequently, the setting-state specifying part 123 specifies the current setting states differing from the standard setting conditions (S4). It should be noted that when the standard setting condition of the light sensitivity of the image sensor 43 is searched in S2, comparison processing is carried out between this standard setting condition and the current electric charge accumulation time. Meanwhile, if the standard setting condition of the light sensitivity of image sensor 43 is not searched in S2, there is no need to carry out comparison processing regarding the electric charge accumulation time.

The controller 101 displays information based on the specified result in S4 (for example, the setting operation screen 170) on the display 103 (S5).

When the tester inputs the instructions for changing the setting states (S6), the controller 101 changes the setting states of respective parts of the device (S7). At this time, the controller 101 changes the electric charge accumulation time of the image sensor 43.

It should be noted that, also in the event of arranging a mechanical shutter in the light path guided to the image sensor 43 in place of the electric shutter for controlling the electric charge accumulation time, a similar process as that mentioned above may be carried out.

(6th Operation Example)

An explanation is provided regarding the operation of the slit lamp microscope 1 carried out using the setting state of the direction of the observation optical axis O1. It should be noted that a configuration is possible in which the direction of the observation optical axis O1 is changed, or the setting state thereof may be used for controlling other configuration parts. Examples of the latter include the 2nd operation example mentioned above.

The direction of the observation optical axis O1 is changed by the controller 101 controlling the observation system turning mechanism 106. Accordingly, the controller 101 recognizes the current setting state of the direction of the observation optical axis O1. It should be noted that when the user manually sets the direction of the observation optical axis O1, the setting state thereof is detected by a sensor.

Hereinafter, an explanation is provided regarding the operation example for controlling the direction of the observation optical axis O1 with reference to the flow chart of the 1st operation example (FIG. 5).

When the observation target site of the eye E is specified by the tester (S1), the searching part 121 searches the standard setting conditions corresponding to the designated site (S2). Here, when the standard setting condition of the direction of the observation optical axis O1 is included in the standard-setting-condition information 110, this is also searched.

The setting-state acquiring part 122 acquires the current setting states of respective parts of the device (S3). At this time, the current setting state of the direction of the observation optical axis O1 is acquired.

Subsequently, the setting-state specifying part 123 specifies the current setting states differing from the standard setting conditions (S4). It should be noted that if the standard setting condition of the direction of the observation optical axis O1 is searched in S2, comparison processing is carried out between this standard setting condition and the current direction of the observation optical axis O1. Meanwhile, if the standard setting condition of the direction of observation optical axis O1 is not searched in S2, there is no need to carry out comparison processing regarding the direction of the observation optical axis O1. The controller 101 displays information based on the specified result in S4 (for example, the setting operation screen 170) on the display 103 (S5).

When the tester inputs the instructions for changing the setting states (S6), the controller 101 changes the setting states of respective parts of the device (S7). At this time, the controller 101 changes the direction of the observation optical axis O1.

[Effect]

Effects of the slit lamp microscope 1 will be explained.

The slit lamp microscope 1 comprises the illumination system 8, the observation system 6, the display 103, the storage 102, the operation part 104, the data processor 120, and the controller 101. The illumination system 8 comprises the light source 51 that outputs illumination light and the slit forming part 54 that forms the slit in which the slit width thereof may be changed. The illumination system 8 irradiates the illumination light that has passed through the slit onto the eye E. Further, the illumination system 8 is capable of changing the amount of light and irradiation angle of the illumination light. The observation system 6 comprises the magnification optical system 32 for changing the observation magnification, and guides the reflected light of the illumination light from the eye E to the image sensor 43 and the eyepiece 37, respectively. The storage 102 stores the standard-setting-condition information 110 in advance. In the standard-setting-condition information 110, the standard setting conditions of the illumination system 8 and/or the observation system 6 are associated with each of the plurality of sites of eye E, it should be noted that the standard setting conditions may be regarding the illumination system 8, regarding the observation system 6, or may include those regarding both of these. The operation part 104 is an example of an "designating part" for designating a site of the eye E, the data processor 120 comprises the searching part 121, the setting-state acquiring part 122, and the setting-state specifying part 123. The searching part 121 searches the standard setting conditions corresponding to the part designated by means of operation part 104 from the standard-setting-condition information 110. The setting-state acquiring part 122 acquires the current setting states of the illumination system 8 and/or the observation system 8. The setting-state specifying part 123 specifies from among the current setting states acquired by the setting-state acquiring part 122, those differing from the standard setting conditions searched by the searching part 121. The controller 101 displays information based on the specified result on the display 103.

According to the slit lamp microscope 1, the parts of the device having current setting states differing from the standard setting conditions corresponding to the designated site (these conditions indicate the setting states of the respective parts of the device recommended upon observation of the concerned site of the eye) can be specified and displayed. Accordingly, it is possible to appropriately and easily carry out setting of the optical system of the device.

Moreover, the controller 101 is configured to display, as information based on the specified result from setting-state specifying part 123, the specified current setting states in a manner differing from the current setting states conforming to the standard setting conditions.

Thereby, the part of the device with the setting state differing from the recommended standard setting condition may be easily understood. Moreover, as in the standard-setting-condition information 110 in FIG. 6, by means of presenting such standard setting conditions themself, this may be informed to the user.

Moreover, the controller 101 is configured such that the current setting states specified by the setting-state specifying part 123 are changed by means of controlling the illumination system 8 and/or the observation system 6 based on the standard setting conditions searched by the searching part 121.

According to such a configuration, the setting state of respective parts of the device may be automatically changed. Accordingly, simplification of the setting operation of the optical system of the device may be promoted. Moreover, prevention of setting error may also be achieved.

Moreover, the slit lamp microscope 1 comprises the moving mechanism 3 that horizontally moves the illumination system 8 and the observation system 6. Further, the setting-state acquiring part 122 acquires the horizontal positions of the illumination system 8 and the observation system 6 as the current setting states of the optical system of the device. Then, the controller 101 changes the current setting states specified by the setting-state acquiring part 122 based on the acquired positions.

According to such a configuration, suitable control may be carried out in accordance with whether the eye E is a left eye or a right eye.

Moreover, the controller 101 displays the setting-changing button 173 for inputting instructions for changing the specified current setting states on the display 103 along with information based on the specified result by the setting-state specifying part 123. Further, the controller 101 changes the specified current setting states in correspondence with the setting-changing button 173 being operated.

According to such a configuration, the user is able to instruct so as to change the setting state of respective parts of the device to the standard setting condition after confirming the displayed standard setting conditions. Moreover, instructions for changing the setting states may be performed after arbitrarily changing the displayed standard setting conditions. Accordingly, the setting states desired by the user may be easily realized without fail.

Moreover, in the standard-setting-condition information 110, the standard setting conditions regarding at least one observation techniques are associated with each of multiple sites of the eye E. Then, the controller 101 displays information based on the specified result by the setting-state specifying part 123 regarding each observation technique associated with the eye site designated by the user.

According to such a configuration, in accordance with not only the site of the eye E but each of various observation techniques, the settings of the optical system of the device may be appropriately and easily carried out. This is very convenient when taking into account the usage of the slit lamp microscope 1 in the medical fields.

MODIFIED EXAMPLES

The embodiments explained above are only examples for realizing the present invention. One attempting to carry out the present invention may appropriately perform arbitrary modifications within the scope of the present invention. Several examples of such modifications are explained in the following. It should be noted that application is possible by appropriately combining any configurations explained in the above embodiments and/or any configurations explained in the following.

Modified Example 1

In the embodiments mentioned above, upon receiving an instruction for changing a setting state from the user, the corresponding changing process is carried out: however, it is not restricted to this. For example, a configuration is possible in which information is displayed based on the specified result by the setting-state specifying part 123 along with carrying out processing of changing to the standard setting conditions.

Modified Example 2

In the event of displaying the current setting states as in the standard-setting-condition information 110 illustrated in FIG. 6, when there is no need to change the setting states (including when these setting states are different from the standard setting conditions), a configuration is possible of performing instruction for changing the setting states after these setting states are designated. Thereby, observation is possible with setting states according to the request of the user.

Modified Example 3

An explanation is provided regarding the modified example regarding the control of the observation magnification. There is restriction on the amount of the illumination light that may be irradiated onto the eye E. Moreover, an examination is preferably carried out for preventing the subject from feeling unnecessary brightness. The following controls may be carried out in view of such circumstances.

When changing the setting of the magnification to the target value, first, low magnification (magnification lower than the intended target) is set with which the amount of light may be small. At this time, the value of the amount of light is also set to less than the intended target. Then, while observing the eye E with this low magnification, alignment of the optical system of the device with respect to the observation target site as well as focusing are carried out. Following these processes, in correspondence with the predetermined trigger, observation is carried out by changing both the magnification as well as the amount of light to the intended target values. It should be noted that, prior to this observation, precise alignment of the optical system of the device with respect to the observation target site as well as precise focusing may be carried out. Moreover, examples of the abovementioned trigger include an inputting instruction using the operation part 104, and a detection of the completion of alignment and/or the completion of focusing.

Modified Example 4

An explanation is provided regarding the modified example related to controlling the slit width. As explained in Modified Example 3, the amount of illumination light with respect to the eye E is preferably suppressed as much as possible. Taking this into consideration, when changing the slit width, the slit width may be gradually changed from a state in which the slit is small (including a state in which the slit is closed) to the intended target slit width. At this time, the amount of illumination light may be gradually reduced in accordance with the increase in slit width. That is, because the brightness of the irradiation field is affected by the amount of illumination light and the slit width, by means of interlocking control of the slit with and the amount of illumination light mentioned above, appropriate brightness of the irradiation field may be maintained, and further, the brightness of the irradiation field may be maintained substantially constant. Similar interlocking controls may be carried out when the user carries out fine adjustment of the slit width.

Modified Example 5

An explanation is provided regarding the modified example related to controlling the diffused plate 60. In the event the diffused plate 60 is arranged in the light path, the illumination light irradiated onto the eye E is not slit light. Accordingly, control may be carried out such that slit light is not used when the diffused plate 60 is used (that is, so as to fully open the slit). In contrast, when slit light is used, control may be carried out such that the diffused plate 60 is removed from the light path.

Moreover, in the event a sensor for detecting slit width is provided, when the diffused plate 60 is used, interlocking of the slit width and the amount of illumination light is also unnecessary; therefore, there is no need to operate this sensor.

Modified Example 6

An explanation is provided regarding the modified example related to controlling the filter 57. Generally, when the filter 57 is arranged in the light path, the amount of illumination light irradiated onto the eye E becomes small. Accordingly, when the filter 57 is arranged in the light path, interlocking control may be carried out so as to increase the amount of illumination light. In contrast, when retracting the filter 57 from the light path, interlocking control may be carried out so as to reduce the amount of illumination light.

In the event a plurality of filters are selectively arranged in the light path, it is possible to preset, based on light transmittance of each filter etc., the amount of change in the amount of illumination light in the event a filter is arranged in the light path. Moreover, a configuration is also possible in which the change in amount of light is detected when a filter is arranged in the light path using a photodetector etc. and the amount of illumination light is changed based on this detection result.

Modified Example 7

An explanation is provided regarding the modified example of the standard-setting-condition information 110. The standard-setting-condition information 110 may be stored in the device in advance (default) or, for example, be different from the default, for example, in accordance with each medical institution, each tester, each subject, each eye, etc.

Moreover, it is also possible to store a plurality of the standard-setting-condition information 110 and selectively use it. For example, if the standard-setting-condition information 110 is stored for each tester, that is, if the tester ID and the standard-setting-condition information 110 are associated with each other and stored, the tester inputs his/her own ID into the device. The controller 101 searches the standard-setting-condition information 110 associated with the input tester ID from the storage 102 and uses this for subsequent processing. Alternatively, when the standard-setting-condition information 110 is selectively used for each eye E, the standard-setting-condition information 110 is associated with patient ID as well as left/right eye information and stored. Patient ID is obtained by, for example, inputting from the operation part 104 or automatically reading out from an electric medical record. The left/right eye information is obtained by inputting from the operation part 104, automatically reading out from an electric medical record, automatically obtaining the position of the moving mechanism 3, etc.

Modified Example 8

An explanation is provided in the modified example related to the display mode of setting operation screen 170. When the settings of respective parts of the device are changed, the controller 101 may change the display mode of the displayed content related to the settings in which the change has been completed. For example, in the standard-setting-condition information 110 illustrated in FIG. 6, when changing the amount of light, the slit width, and the illuminating angle, once changing the setting of the amount of light is complete, the display content related to the amount of light (the standard setting condition of the amount of light indicated in the setting-content displaying part 172) is deleted: once changing the setting of the slit width is complete, display content related to the slit width (the standard setting condition of the slit width) is deleted: and once changing the setting of the illuminating angle is complete, display content related to the illuminating angle (the standard setting condition of the illuminating angle) is deleted. According to such a configuration, it is possible to easily understand change in which setting states has been completed from among the setting states subject to change, or whether or not change in all setting states has been completed.

Modified Example 9

Various attachment lenses are used in examinations using a slit lamp microscope. For example, a gonioscope is attached to a cornea upon observation of the corner angle and a three-sided mirror is attached to a cornea upon observation of a retina. Moreover, upon observation of a retina, there are cases in which a front lens is used by being arranged without contacting the eye E. The front lens is arranged between the eye E and the mirror 12.

When designating the observation target site or instead of designating the observation target site, presence or absence of using the attachment lens and/or the type thereof are input. The controller 101 may specify the observation target site and/or observation technique in accordance with this input content. It is also possible to detect whether or not the attachment lens is used. This detection process may be carried out by a sensor for detecting the attachment lens (the position thereof) and/or image processing etc. for detecting the change in images when the attachment lens is arranged in the light path.

EXPLANATION OF SYMBOLS

1 slit lamp microscope
3 moving mechanism
6 observation system
8 illumination system
32 magnification optical system
43 image sensor
51 light source
54 slit forming part
56 illumination diaphragm
57 filter
60 diffused plate
70 background light source
100 computer
101 controller
102 storage
103 display
104 operation part
110 standard-setting-condition information
12 data processor
121 searching part
122 setting-state acquiring part
123 setting-state specifying part
132 power-varying mechanism
156 diaphragm driving mechanism
157 filter driving mechanism
160 diffused plate driving mechanism
170 setting operation screen
171 observation-target-site displaying part
172 setting-content displaying part
173 setting-changing button
O1 observation optical axis
O2 illumination optical axis
E eye

What is claimed is:
1. A slit lamp microscope, comprising:
an illumination system configured to include: a light source that outputs illumination light; a slit forming part that forms a slit capable of changing the slit width; a diffusion member that is capable of inserting into and removed from a light path of the illumination light and diffuses the illumination light; and a filter that is capable of inserting into and removed from the light path, wherein the illumination light having passed through the slit is irradiated to an eye and the amount as well as the irradiation angle of the illumination light are changeable,
a background illumination system configured to irradiate background illumination light to a peripheral region of an irradiation field of the illumination light;
an observation system configured to include a magnification optical system for changing observation magnification, and guide reflected light of the illumination light from the eye to each of an image sensor and an eyepiece;
a display;
a storage configured to store correspondence information that associates, with each of multiple sites of an eye, standard setting conditions regarding at least one of: a value of the observation magnification; a value of the slit width; a value of the light amount of the illumination light; a value of the irradiation angle; the presence or absence of irradiation of the background illumination light; the presence or absence of the diffusion member in the light path; and the presence or absence of the filter in the light path;
a designating part configured to designate a site of the eye;
a searching part configured to search the standard setting conditions corresponding to the designated site from the correspondence information;
an acquiring part configured to acquire current setting states regarding at least one of: a value of the observation magnification; a value of the slit width; a value of the light amount of the illumination light; a value of the irradiation angle; the presence or absence of irradiation of the background illumination light; the presence or absence of the diffusion member in the light path; and the presence or absence of the filter in the light path;
a specifying part configured to specify, from among the acquired current setting states, those differing from the searched standard setting conditions; and
a controller configured to display information based on the specified result by the specifying part on the display.
2. A slit lamp microscope, comprising:
an illumination system configured to include a light source that outputs illumination light and a slit forming part that forms a slit capable of changing the slit width, wherein the illumination light having passed through the slit is irradiated to an eye and the amount as well as the irradiation angle of the illumination light are changeable;
an observation system configured to include a magnification optical system for changing observation magnification, and guide reflected light of the illumination light from the eye to each of an image sensor and an eyepiece;
a display;
a storage configured to store correspondence information that associates, with each of multiple sites of an eye, standard setting conditions of the illumination system and/or the observation system;
a designating part configured to designate a site of the eye;

a searching part configured to search the standard setting conditions corresponding to the designated site from the correspondence information;
an acquiring part configured to acquire current setting states of the illumination system and/or the observation system;
a specifying part configured to specify, from among the acquired current setting states, those differing from the searched standard setting conditions; and
a controller configured to display information based on the specified result by the specifying part on the display.

3. The slit lamp microscope according to claim 1 or claim 2, wherein the controller displays, as the information based on the specified result, the specified current setting states in a different manner from the current setting states that coincide with the standard setting conditions.

4. The slit lamp microscope according to claim 1 or claim 2, wherein the controller controls the illumination system and/or the observation system based on the searched standard setting conditions, thereby changing the specified current setting states.

5. The slit lamp microscope according to claim 4, comprising a moving mechanism configured to horizontally move the illumination system and the observation system, wherein
the acquiring part acquires the horizontal positions of the illumination system and the observation system as the current setting states, and
the controller changes the specified current setting states based on the acquired positions.

6. The lamp microscope according to claim 4, wherein
the controller displays, together with the information based on the specified result, an operation key used for inputting instructions for changing the specified current setting states on the display, and
the controller changes the current setting states in accordance with the operation key being operated.

7. The slit lamp microscope according to claim 1 or claim 2, wherein
in the correspondence information, the standard setting conditions regarding at least one observation technique are associated with each of the multiple sites, and
the controller displays the information based on the specified result for each observation technique associated with the designated site.

8. The slit lamp microscope according to claim 2, wherein
in the correspondence information, the standard setting conditions regarding at least one from among the value of the observation magnification, the value of the slit width, the value of the light amount of the illumination light, and the value of the irradiation angle are associated with each of the multiple sites, and
the acquiring part acquires the current setting states regarding each of: the value of the observation magnification, the value of the slit width, the value of the light amount of the illumination light, and the value of the irradiation angle.

9. The slit lamp microscope according to claim 8, wherein
the illumination system includes a diffusion member that is capable of inserting into and removed from a light path of the illumination light and diffuses the illumination light,
in the correspondence information, the standard setting conditions regarding the presence or absence of the diffusion member in the light path are associated with each of the multiple sites, and
the acquiring part acquires the current setting states regarding the presence or absence of the diffusion member in the light path.

10. The slit lamp microscope according to claim 8, comprising a background illumination system configured to irradiate background illumination light to a peripheral region of an irradiation field of the illumination light, wherein
in the correspondence information, the standard setting conditions regarding the presence or absence of irradiation of the background illumination light are associated with each of the multiple sites, and
the acquiring part acquires the current setting states regarding the presence or absence of irradiation of the background illumination light.

11. The slit lamp microscope according to claim 8, wherein
the illumination system includes a filter that is capable of inserting into and removed from the light path,
in the correspondence information, the standard setting conditions regarding the presence or absence of the filter in the light path are associated with each of the multiple sites, and
the acquiring part acquires the current setting states regarding the presence or absence of the filter in the light path.

12. The slit lamp microscope according to claim 1 or claim 8, wherein
the illumination system includes an illumination diaphragm capable of changing the diaphragm value,
in the correspondence information, the standard setting conditions regarding the diaphragm value are associated with each of the multiple sites, and
the acquiring part acquires the current setting states regarding the diaphragm value.

13. The slit lamp microscope according to claim 1 or claim 8, wherein
in the correspondence information, the standard setting conditions regarding light sensitivity of the image sensor are associated with each of the multiple sites, and
the acquiring part acquires the current setting states regarding the light sensitivity.

14. The slit lamp microscope according to claim 1 or claim 8, wherein
in the correspondence information, the standard setting conditions regarding electric charge accumulation time of the image sensor are associated with each of the multiple sites, and
the acquiring part acquires the current setting states regarding the electric charge accumulation time.

15. The slit lamp microscope according to claim 1 or claim 8, wherein
the direction of the optical axis of the observation system can be changed,
in the correspondence information, the standard setting conditions regarding the direction of the optical axis are associated with each of the multiple sites, and
the acquiring part acquires the current setting states regarding the direction of the optical axis.

* * * * *